US00PP10667P

United States Patent [19]

Zary

[11] Patent Number: Plant 10,667

[45] Date of Patent: Nov. 3, 1998

[54] HYBRID TEA ROSE PLANT NAMED 'JACOSCH'

[75] Inventor: Keith W. Zary, Thousand Oaks, Calif.

[73] Assignee: Bear Creek Gardens, Inc., Medford, Oreg.

[21] Appl. No.: 800,659

[22] Filed: Feb. 14, 1997

[51] Int. Cl.[6] ..... A01H 5/00

[52] U.S. Cl. ..... Plt./14

[58] Field of Search ..... Plt./14

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the Hybrid Tea class, having attractive clear white blooms; long stems; excellent cut flower production; and long vase life.

1 Drawing Sheet

The present invention relates to a new and distinct variety of rose plant of the hybrid tea class which was originated by me by crossing the variety ARObipy, U.S. Plant Pat. No. 6,714, with the variety Osiana, U.S. Plant Pat. No. 7,660.

The primary objective of this breeding was to produce a new rose variety having the white flower color of the female parent combined with the large flower size and long stems of the male parent. The objective was substantially achieved, along with other desirable improvements, as evidenced by the following unique combination of characteristics that are outstanding in the new variety and that distinguish it from its parents, as well as from all other varieties of which I am aware:

1. Attractive clear white hybrid tea blooms;
2. Long stems (24–28 inches)
3. Good production (180–190 stems per square meter of greenhouse)
4. Good vase life.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—ARObipy (U.S. Plant Pat. No. 6,714).

*Pollen parent*.—Osiana (U.S. Plant Pat. No. 7,660).

Classification:

*Botanical*.—*Rosa hybrida*.

*Commercial*.—Hybrid tea.

FLOWER

Observations made from specimens grown in a greenhouse environment at Somis, Calif. from March 1996 to January 1997.

Blooming habit: Recurrent.

Bud:

*Size*.—2 inches long when the petals start to unfurl.

*Form*.—The bud form is long, pointed ovoid.

*Color*.—When sepals first divide, bud color is Green-White Group 157C. When half blown, the upper sides of the petals are White Group 155D; and the lower sides of the petals are White Group 155D.

*Sepals*.—Color: Green Group 138B. Surface texture: Covered in fine hairs. There are three normally appendaged sepals. There are two unappendaged sepals with hairy edges.

*Receptacle*.—Color: Green Group 137D. Shape: Apple. Size: Medium (⅜×¼ inch). Surface: Smooth.

*Peduncle*.—Length: Medium (2½ to 3 inches). Surface: Glandular. Color: Medium green. Strength: Stiff, erect.

Bloom:

*Size*.—Large. Average open size is 4½ to 5 inches.

*Borne*.—Singly.

*Stems*.—Long, strong. Average length is about 24 to 28 inches.

*Form*.—When first open: High centered Permanence: Retains its form to the end.

*Petalage*.—Number of petals under normal conditions: 30 to 35.

*Color*.—The upper sides of the petals are White Group 155D. The reverse sides of the petals are white Group 155D. The base of each petal has a very small (⅛ ×⅛ inch) greenish half-moon at the point of attachment. The major color on the upper side is White Group 155D.

*Variegations*.—Occasional greenish white streak on the guard petals.

*Discoloration*.—No change through the entire life of the flower.

*Fragrance*.—Moderate.

Petals:

*Texture*.—Thick.

*Shape*.—Round.

*Form*.—Tips slightly recurved, edges slightly quilled.

*Arrangement*.—Imbricated, with a few petaloids in the center.

*Persistence*.—Drop off cleanly.

*Lastingness*.—On the plant: Long (7 days). As a cut flower: Long (10 days).

Reproductive parts:

*Anthers*.—Size: Medium. Quantity: Many. Color: Yellow. Arrangement: Regular around styles.

*Filaments*.—Color: Yellowish; white with some pink.

*Pollen*.—Color: Gold yellow.

*Styles*.—Color: Red.

*Stigmas*.—Color: Greenish white.

Form: Bush.
Growth: Very vigorous.
Foliage:
*Number of leaflets on normal mid-stem leaves.*—
*Size.*—Large (6×4½ inches).
*Quantity.*—Normal. *Color.*—New foliage: Greyed-Orange Group 178C but very quickly turning green.
Old foliage: Upper surface is Green Group 137A; lower surface is Green Group 138B.
Leaflets:
*Shape.*—Pointed oval.
*Texture.*—Upper side: Leathery.
*Edge.*—Serrated.
*Serration.*—Single.
*Petiole rachis.*—Color: Reddish when young, then green.
*Petiole underside.*—Rough, with prickles.
*Stipules.*—Medium (½ inch), serrated, bearded.
*Disease resistance.*—Resistant to mildew under normal growing conditions at Somis, Calif. Not tested for rust or blackspot.

Wood:
*New wood.*—Color: Light green. Bark: Smooth.
*Old wood.*—Color: Green. Bark: Smooth.
Prickles:
*Quantity.*—On main canes from base: Ordinary. On laterals from main canes: Ordinary.
*Form.*—Medium (⅜ inch), hooked slightly downward.
*Color when young.*Red.
Small prickles:
*Quantity.*—On main stalks: None. On laterals: None.

I claim:

1. A new and distinct variety of rose plant of the Hybrid Tea class, substantially as herein shown and described, characterized particularly as to novelty by the unique combination of its attractive clear white blooms; long stems; excellent cut flower production; and long vase life.

* * * * *

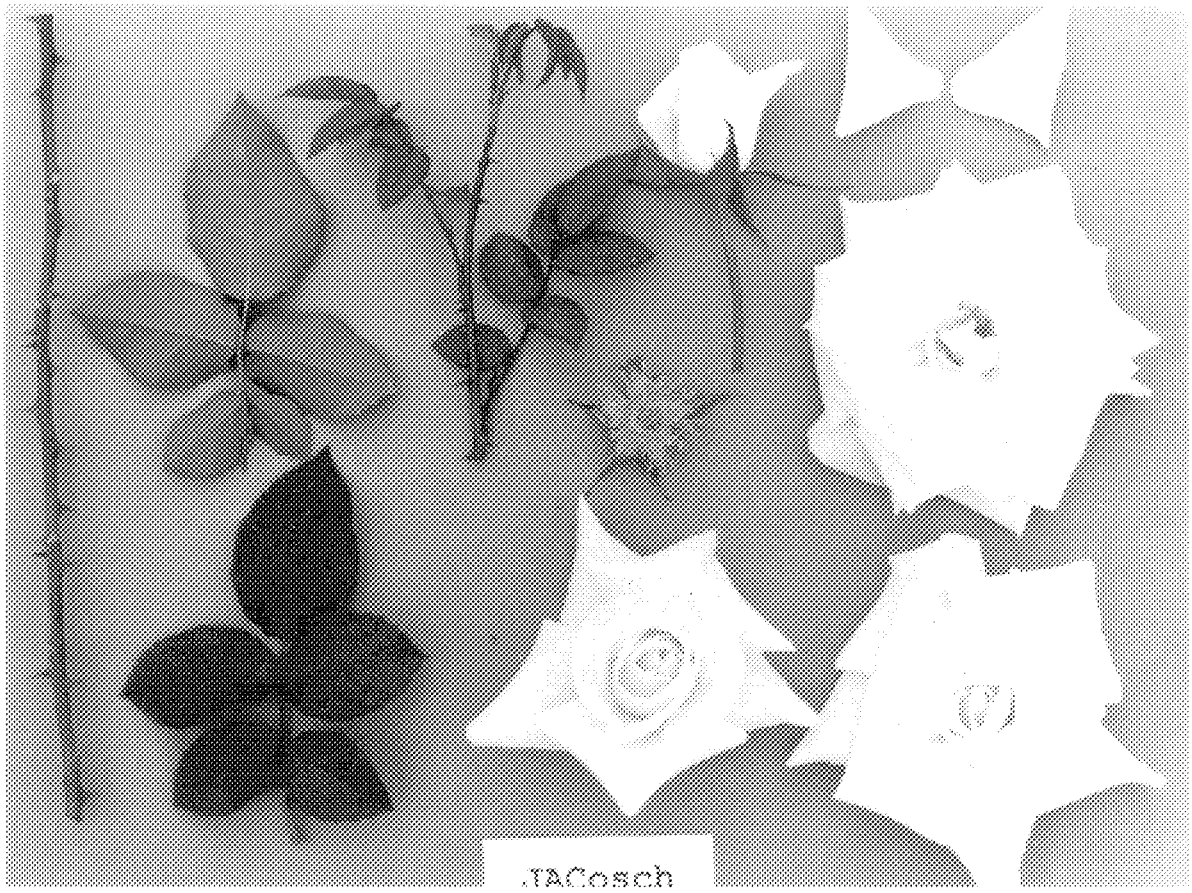
JACosch

UNITED STATES PATENT AND TRADEMARK OFFICE

CERTIFICATE OF CORRECTION

PATENT NO. : PP 10,667
DATED : November 3, 1998
INVENTOR(S) : Keith Zary

It is certified that error appears in the above-indentified patent and that said Letters Patent is hereby corrected as shown below:

Column 3, line 4, delete "leaves." and insert --leaves: 5.--
Column 4, line 8, delete "young.Red." and insert --young: Red.--

Signed and Sealed this

Twelfth Day of October, 1999

*Attest:*

Q. TODD DICKINSON

*Attesting Officer*

*Acting Commissioner of Patents and Trademarks*